United States Patent
Gradel (10) Patent No.: US 8,882,849 B2
(45) Date of Patent: Nov. 11, 2014

(54) ACETABULAR CUP WITH HIGH RETENTION CAPACITY

(75) Inventor: Thomas Gradel, Marignier (FR)

(73) Assignee: Inventorio SA, Gland (CH)

( * ) Notice: Subject to any disclaimer, the term of this patent is extended or adjusted under 35 U.S.C. 154(b) by 122 days.

(21) Appl. No.: 13/500,927

(22) PCT Filed: Oct. 12, 2010

(86) PCT No.: PCT/IB2010/054603
§ 371 (c)(1),
(2), (4) Date: Apr. 9, 2012

(87) PCT Pub. No.: WO2011/045737
PCT Pub. Date: Apr. 21, 2011

(65) Prior Publication Data
US 2012/0197412 A1    Aug. 2, 2012

(30) Foreign Application Priority Data
Oct. 12, 2009   (FR) ...................................... 09 57130

(51) Int. Cl.
*A61F 2/30* (2006.01)
*A61F 2/32* (2006.01)
*A61F 2/34* (2006.01)
*A61F 2/00* (2006.01)

(52) U.S. Cl.
CPC ......... *A61F 2/32* (2013.01); *A61F 2002/30612* (2013.01); *A61F 2002/3493* (2013.01); *A61F 2220/0025* (2013.01); *A61F 2002/3241* (2013.01); *A61F 2220/0033* (2013.01); *A61F 2/0095* (2013.01); *A61F 2002/305* (2013.01); *A61F 2002/30332* (2013.01); *A61F 2002/3208* (2013.01); *A61F 2002/3233* (2013.01)

USPC .................. 623/22.11; 623/23.4; 623/23.41; 623/22.15

(58) Field of Classification Search
CPC .. A61F 2002/3411; A61F 2/32; A61F 2/4241
USPC .................................... 623/16.11, 22.11–22.2
See application file for complete search history.

(56) References Cited

U.S. PATENT DOCUMENTS

| | | | | |
|---|---|---|---|---|
| 4,676,798 A | * | 6/1987 | Noiles | 623/22.18 |
| 2003/0060890 A1 | * | 3/2003 | Tarabishy | 623/22.12 |
| 2005/0060040 A1 | | 3/2005 | Auxepaules | |
| 2008/0015707 A1 | * | 1/2008 | Lambert et al. | 623/22.17 |
| 2010/0191244 A1 | * | 7/2010 | White et al. | 606/88 |
| 2010/0331992 A1 | * | 12/2010 | Podolsky | 623/22.15 |

FOREIGN PATENT DOCUMENTS

| | | |
|---|---|---|
| DE | 4102510 A1 | 7/1992 |
| FR | 2876278 A1 | 4/2006 |
| WO | 8807845 A1 | 10/1988 |

* cited by examiner

*Primary Examiner* — Jason-Dennis Stewart
(74) *Attorney, Agent, or Firm* — William H. Eilberg (57) ABSTRACT

An acetabular cup includes an articular insert (1) having a substantially semi-spherical articular cavity (1*c*), and a spherical head (2) engaged in the articular cavity (1*c*). A retaining device (10*a*) opposes the axial release (4) of the spherical head (2) from the articular cavity (1*c*) of the articular insert (1). For example, the retaining device can take the form of a back-tapered segment (10*a*) of the articular insert (1). The spherical head (2) is factory mounted in the articular insert (1), by temporarily heating the articular insert (1) and performing sterilization after assembly. In this way, the spherical head (2) retention capacity in the articular insert (1) is increased substantially in order to reduce the risk of luxation.

10 Claims, 11 Drawing Sheets

ACETABULAR CUP WITH HIGH RETENTION CAPACITY

TECHNICAL FIELD OF THE INVENTION

The present invention relates to a prosthetic acetabulum for replacing the natural acetabulum of the hip.

A total hip prosthesis comprises two parts constituting a ball-and-socket joint, namely a first part intended to be implanted in the pelvis of a patient, and a second part intended to be implanted in the femur.

The first part of the prosthesis generally has a stem which is intended to engage in the medullary canal of the femur, and of which the proximal end is connected by a neck to a spherical head intended to engage in the female part of the joint.

The second part of the prosthesis, which has to be implanted in the pelvis, and which will be designated generally by the word acetabulum, normally comprises a hemispherical insertion cup, which is placed in a prepared cotyloid cavity of the pelvic bone, and in which is placed an articular insert, which is designed to receive the spherical head. The insertion cup is commonly made of metal. The articular insert is made of a material with a low coefficient of friction, such as polyethylene or a ceramic.

In the known devices, a distinction can be made between single-mobility acetabulums, dual-mobility acetabulums, and acetabulums with a movable cup.

In the single-mobility acetabulums, the polyethylene or ceramic insert is fixed in an insertion cup and has a coaxial and substantially hemispherical articular cavity permitting the engagement and pivoting of the spherical head of the first part of the prosthesis.

The rotation movements of the joint then take place between the spherical head of the first part of the prosthesis and the articular cavity of the articular insert.

In a dual-mobility acetabulum, the articular insert is itself mounted rotatably in the insertion cup, thereby providing a first sliding surface between the insertion cup and the articular insert, and a second sliding surface between the articular insert and the spherical head.

In the acetabulums with a movable cup, the articular insert made of ceramic has a spherical outer surface so as to be rotatably mounted directly in the cotyloid cavity of the pelvis of a patient. Alternatively, an articular insert made of polyethylene is engaged fixedly in a metal cup which has a spherical outer surface and is itself mounted rotatably in the cotyloid cavity of the pelvis of a patient.

Therefore, the main problem during use of a hip prosthesis is the risk of luxation. Luxation means the release of the spherical femoral head from the articular cavity.

Various means have already been proposed for reducing the risks of luxation.

For example, dual-mobility acetabulums have the effect of slightly reducing the risk of luxation. However, this reduction is insufficient.

An additional means for reducing the risks of luxation has been proposed in the form of an increase in the depth of the articular cavity of the articular insert, such that the head is engaged across a spherical cap slightly larger than the hemisphere. In practice, it is then necessary to engage the head with force in the articular cavity, and this requires a specific tool of the press type.

Hitherto, the spherical heads of the male part of the joint have formed an interchangeable element which is attached to the end of the neck and which allows the practitioner, when implanting the prosthesis, to easily adapt the diameter of the head and the length of the neck by simply selecting a suitable head from among a series of heads with different diameters and with seats of different depths in which the neck end is engaged. The choice of head by the practitioner is necessarily made according to the specific anatomical features presented by the patient receiving the prosthesis.

This means that it is therefore the practitioner who then has to engage the head with force in the articular cavity of the articular acetabulum, by means of the tool of the press type. This operation of engagement with force poses considerable risks of damaging the outer surface of the head and the inner surface of the articular insert, such that the articular surfaces are then degraded, thus reducing the lifetime of the prosthesis.

In addition, since this is an operation carried out by the practitioner in the operating theater, using a relatively basic tool of the press type, the admissible force for engaging the head in the cavity of the articular acetabulum is necessarily limited, and this at the same time limits the retention capacity of the head in the articular insert. There is therefore still a need to increase this retention capacity.

The teaching of document DE 41 02 510 A1 discloses increasing the force by which the head is retained in the articular insert by providing a retaining means in the form of a continuation of the acetabulum, which increases the angle of its cavity beyond 180°, on a portion of its periphery. However, the document does not describe a solution to the resulting difficulty of introducing the head.

Alternatively, it has been proposed to increase the force of retention of the head in the articular insert by fitting a retaining ring in a groove formed at the entrance of the cavity of the articular insert. The ring is made of polyethylene. It can be slit or can have snap-fit means, as are described in the document WO 88/07845 A1. By virtue of its transverse slit or its snap-fit means, and since polyethylene is a relatively elastic material, the ring can be easily deformed by reducing its diameter in order to introduce it into the entrance of the cavity, and it is then relaxed such that it recovers its initial diameter and engages with its periphery in the corresponding groove of the articular insert. The ring then opposes the withdrawal of the head from the articular insert. However, there is still a risk of the retaining ring itself being ejected in the event of a force tending to withdraw the head from the articular insert, this being due to the flexibility of the ring, which is a result of the presence of the transverse slit. Consequently, the retention capacity is still insufficient.

SUMMARY OF THE INVENTION

The invention results from the observation that all the means available to the practitioner in the operating theater for fitting the head in the articular insert do not permit a sufficient retention capacity, and it appears that sterilization has a negative influence on this retention capacity.

The problem addressed by the present invention is that of substantially reducing the risk of luxation of a hip prosthesis by providing the acetabulum with a very much increased retention capacity, so as to eliminate any risk of luxation, by avoiding the negative influence that sterilization has on this retention capacity.

In order to achieve these aims, and others, the invention thus proposes a prosthetic hip acetabulum, comprising:
  an articular insert, with a receiving face in which is opened a cavity with a substantially hemispherical, concave articular surface,
  a spherical head, which can be engaged in the articular cavity of the articular insert, a retaining means for opposing the axial release of the spherical head from the articular cavity of the articular insert when it is engaged in the articular cavity, in which:

the assembly composed of articular insert and spherical head is packed in a sterile state in a protective envelope, and, in the protective envelope, the spherical head is engaged in the articular cavity of the articular insert and is retained by the retaining means.

This arrangement makes it possible to assemble the acetabulum at the time of manufacture in the factory and to perform the sterilizing step after the assembly step involving fitting the spherical head in the articular insert. It has been found, according to the present invention, that the assembly step, involving forced engagement of one element in another, reduces the mechanical properties of at least one of the two elements if it is made of polyethylene or another equivalent plastic material and if it has been subjected beforehand to a sterilizing step. Thus, performing the sterilizing step after assembly avoids damaging the mechanical properties of the element and increases the retention capacity of the head in the articular insert.

The increase in the retention capacity has been able to be demonstrated in tests, of which the results are set out later in the description.

In practice, by virtue of these arrangements, the force retaining the spherical head and exerted by the retaining means can be greater than a defined force threshold, this force threshold being considerably greater than the retention force obtained by the currently known devices, for given materials and given geometries of the elements forming the prosthesis.

According to a first embodiment, in the articular cavity and the retaining means, the spherical head is engaged across a spherical cap larger than the hemisphere.

The spherical cap can advantageously extend by an angle greater than 190°.

In this way, the retaining means can be formed by the articular insert itself, which is made of polyethylene or another equivalent plastic material and has a retaining segment undercut in the articular surface.

In this case, the articular insert can also have an outer surface in the shape of a spherical cap in order to be mounted rotatably in an insertion cup and in order thereby to constitute a dual-mobility acetabulum.

According to another embodiment, the retaining means comprises a continuous annular ring, having a retaining surface in the shape of a spherical crown and able to engage functionally with play against the spherical head, and having peripheral fixing projections able to interlock functionally with corresponding recesses of the articular insert or with corresponding recesses of a peripheral cup surrounding the articular insert, in order to prevent withdrawal of the continuous annular ring.

The absence of a transverse slit in the continuous annular ring provides the ring with great stiffness, which avoids the risk of withdrawal of the ring itself in the event of the spherical head being withdrawn from the articular insert.

In this case, the continuous annular ring can advantageously be made of polyethylene or of another equivalent plastic material.

On account of the continuous nature of the annular ring constituting the retaining means in the second embodiment, and on account of the angle of more than 190° of the spherical cap across which the head is engaged in the articular cavity and the retaining means, a high retention capacity of the spherical head in the articular insert is achieved.

According to the invention, this retention capacity is increased still further by making available a method of assembly for producing a prosthetic hip acetabulum according to the invention, with a spherical head engaged in a cavity of an articular insert and retained by a retaining means, the method having a step of sterilizing the components of the acetabulum and an assembly step involving fitting the spherical head in the articular insert and the retaining means, in which method the sterilizing step is performed after the assembly step.

To further reduce or to avoid deterioration of the mechanical properties of the elements to be assembled upon engagement of the head in the articular insert and the retaining means, it is possible, during the assembly step, for the retaining means to be subjected advantageously to a differential thermal stress which temporarily modifies its dimensions in order to facilitate assembly, and then, after assembly, the retaining means is allowed to return to room temperature so as to oppose the withdrawal of the spherical head from the articular insert.

In this method, according to a first embodiment:

the retaining means is the articular insert itself, which is made of polyethylene or another equivalent plastic material, the differential thermal stress involves heating the articular insert in order to increase its internal diameter and thereby facilitate the axial introduction of the spherical head.

In this method, according to another embodiment:

the retaining means is a continuous annular ring made of polyethylene or another equivalent plastic material, the differential thermal stress involves cooling the continuous annular ring in order to reduce its internal diameter and thereby facilitate the engagement of the peripheral projections of the ring in the corresponding recesses of the articular insert or of the peripheral cup.

BRIEF DESCRIPTION OF THE DRAWINGS

Other objects, features and advantages of the present invention will become clear from the following description of particular embodiments, with reference being made to the attached figures in which.

DESCRIPTION OF PREFERRED EMBODIMENTS

Reference is made to FIGS. 1 to 12, which illustrate the structure of a dual-mobility prosthetic acetabulum according to a first embodiment of the present invention.

Figure 1:
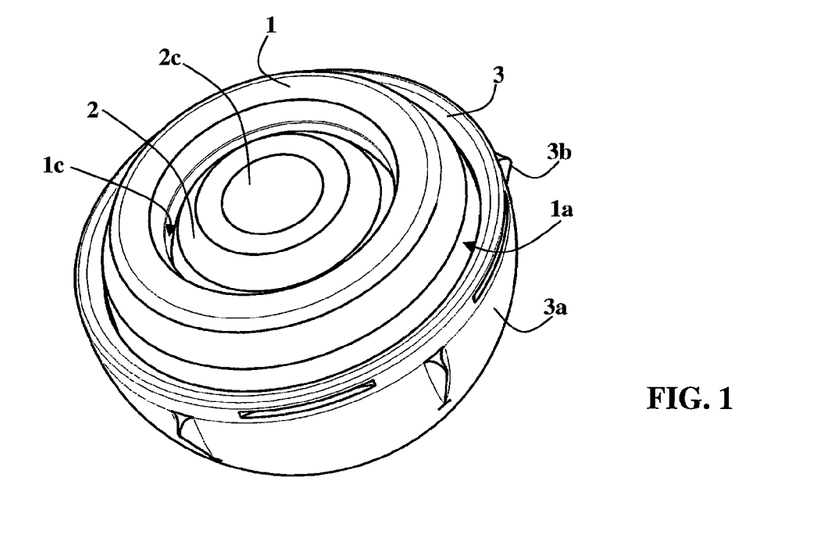
FIGS. 1 to 3 illustrate, in a perspective view, a front view and a lateral cross section, respectively, a prosthetic hip acetabulum according to a first embodiment of the present invention.
Figure 2:
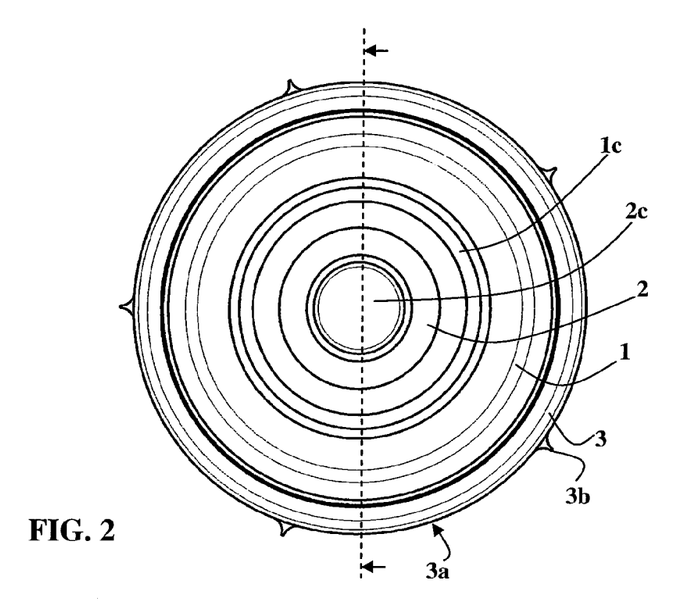
Figure 3:
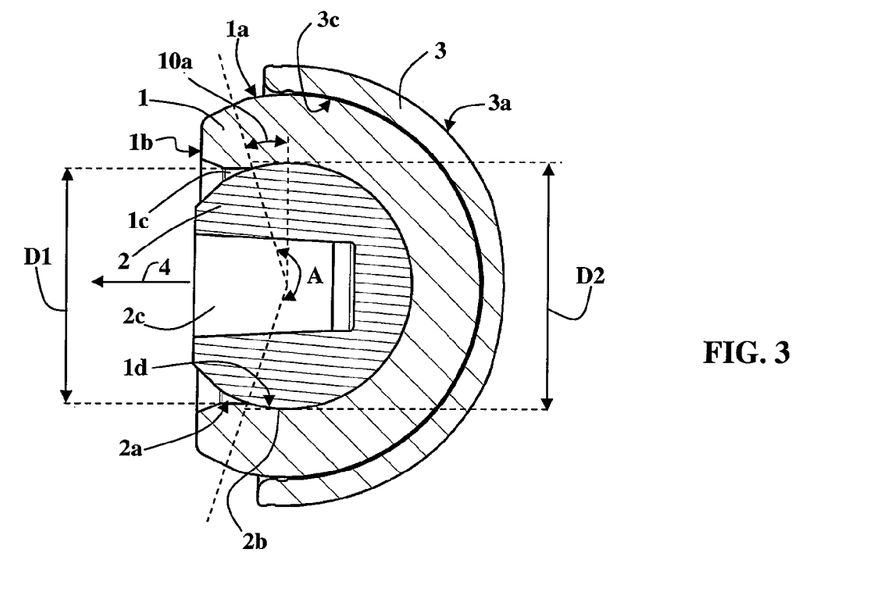

After complete assembly, the prosthetic acetabulum is as illustrated in FIGS. 1 to 3. It comprises an articular insert 1, a spherical head 2, and an insertion cup 3.

The insertion cup 3 is made of metal. It has a convex outer anchoring face 3a which is substantially hemispherical and is designed to be anchored in a cotyloid cavity in the pelvis of a patient. As will be seen more clearly in FIGS. 1 and 2, the outer anchoring face advantageously has projections 3b to facilitate its anchoring in the cotyloid cavity of the pelvis. The insertion cup 3 has an inner receiving face 3c of spherical shape which is mirror-polished to constitute an articulation surface receiving the articular insert 1. The articular insert 1 is made of polyethylene or another equivalent plastic material. It has a spherical outer face 1a engaging in the inner receiving face 3c of the insertion cup 3 in order to permit the pivoting of the articular insert 1 in the insertion cup 3. The articular insert 1 has a receiving face 1b, in which is opened an articular cavity 1c with a substantially hemispherical concave articular surface 1d.

The spherical head 2 is engaged in the articular cavity 1c of the articular insert 1, in which it is retained by a retaining means that opposes its axial release under the effect of an extraction force illustrated by the arrow 4.

In this embodiment, the retaining means is formed by the articular insert 1 itself, which for this purpose has an articular surface 1d extending by an angle A greater than 190°. On account of the value of the angle A being greater than 190°, the articular surface 1d has an undercut segment 10a, which narrows toward the receiving face 1b. This has the result that the diameter D1 of the opening of the articular insert 1 is smaller than the diameter D2 of the spherical head 2, which can therefore be released from the articular cavity 1c only under the effect of an extraction force 4 above a high value.

The spherical head 2 has a spherical outer articular surface 2a, which is thus engaged in the articular cavity 1c across a spherical cap 2b larger than the hemisphere and which extends by the angle A.

The spherical head 2 can be made of ceramic or of metal. Metal will be preferred for reasons of cost. The metal can be stainless steel or titanium, for example. The same applies to the insertion cup 3.

The spherical head 2 has a frustoconical recess 2c for receiving, with force, a neck end of the first part of a hip prosthesis.

Figure 4:
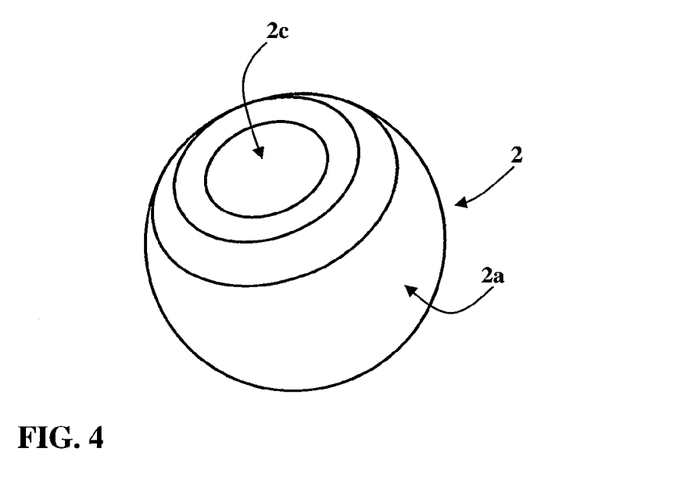
FIGS. 4 to 6 illustrate, in a perspective view, a front view and a lateral cross section, a spherical head such as the one from the embodiment in FIGS. 1 to 3.
Figure 5:
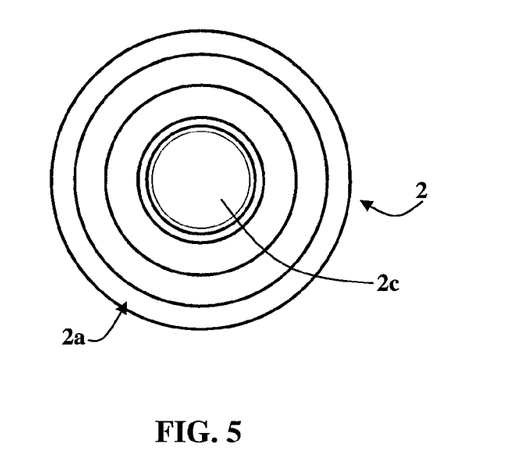
Figure 6:
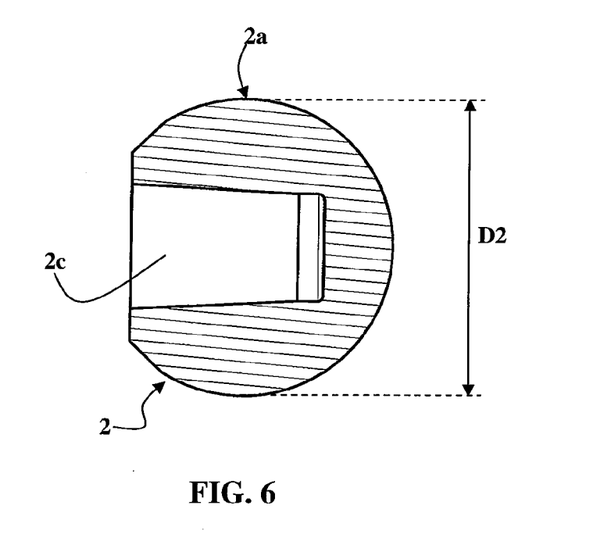

FIGS. 4 to 6 show more clearly the structure of the spherical head 2, isolated from the other elements of the acetabulum. The same elements are designated by the same reference numbers as in FIGS. 1 to 3.

Figure 7:
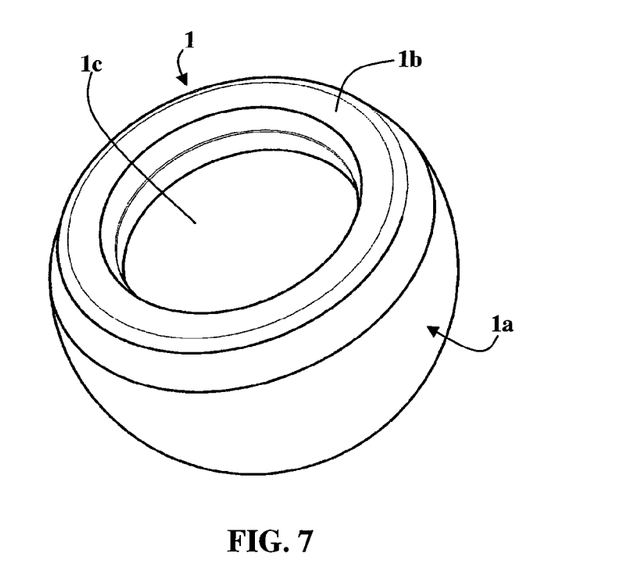
FIGS. 7 to 9 illustrate, in a perspective view, a front view and a lateral cross section, respectively, the articular insert of the prosthetic acetabulum from FIGS. 1 to 3.
Figure 8:
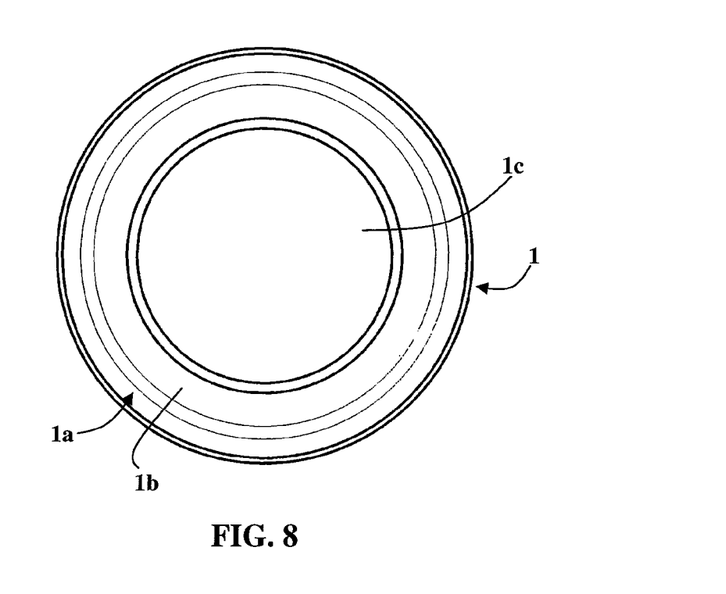
Figure 9:
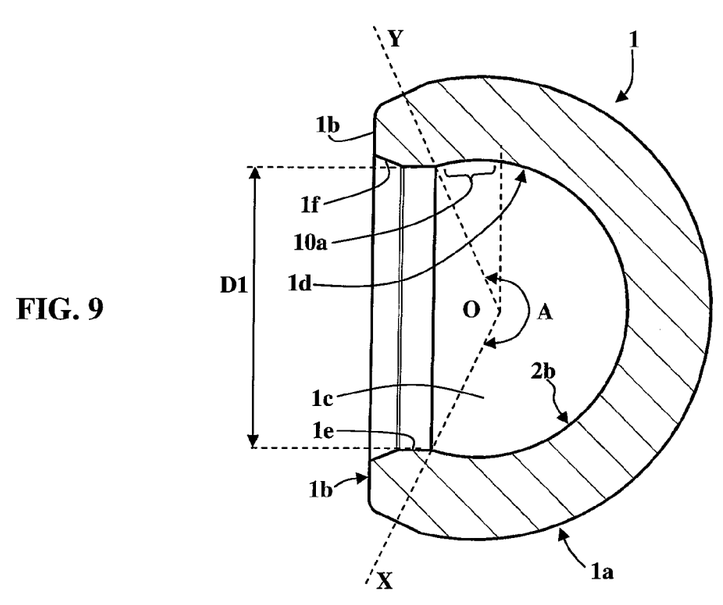

FIGS. 7 to 9 show more clearly the structure of the articular insert 1, isolated from the other elements of the acetabulum. The same elements are designated by the same reference numbers as in FIGS. 1 to 3.

FIG. 9 shows more clearly the articular surface 1d, and the portion thereof corresponding to the spherical cap 2b, limited by a cone whose summit is at the center O of the spherical head 2 and of the articular surface 1d and which is indicated by the lines OX and OY. This spherical cap 2b is larger than the hemisphere, and it extends by the angle A or the angle at which the spherical head 2 is engaged in the articular insert in FIG. 3. At right angles to the intersection with the cone OX-OY, the articular surface 1d is continued by a cylindrical segment 1e of diameter D1, then by a beveled edge joining the receiving face 1b.

Figure 10:
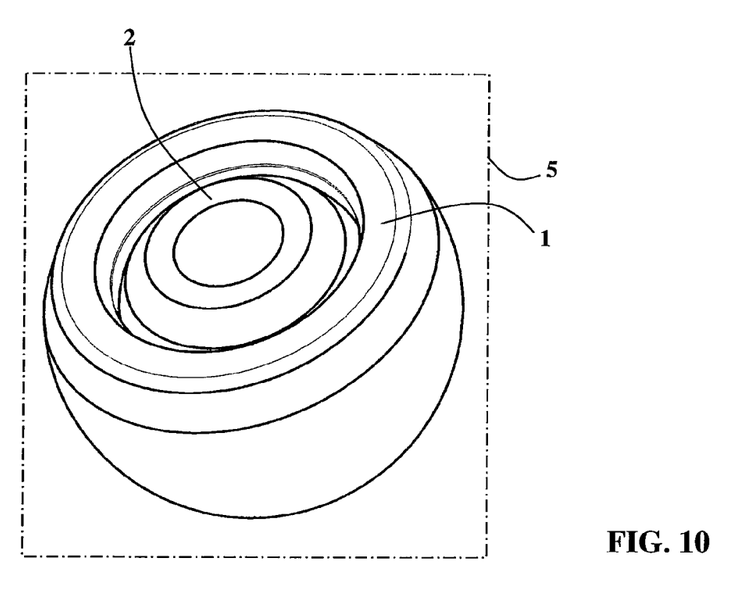
FIGS. 10 to 12 illustrate, in a perspective view, a front view and a lateral cross section, respectively, the assembled unit composed of articular insert and spherical head, packed in a sterile state in a protective envelope for its distribution to the place of use.
Figure 11:
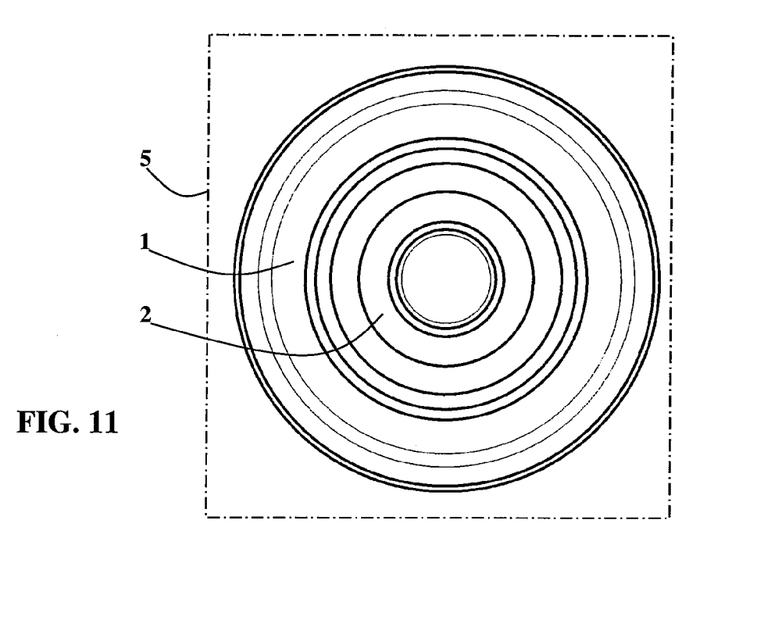
Figure 12:
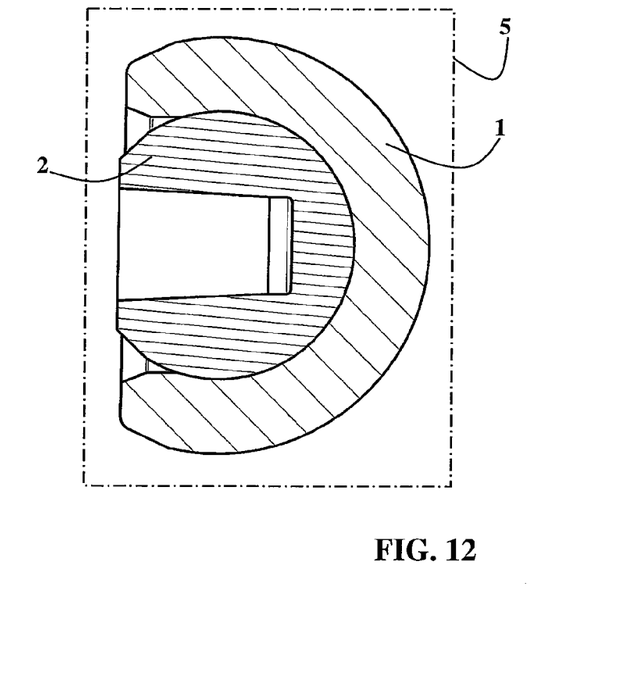

According to the invention, the articular insert 1 and the spherical head 2 are factory-assembled and are then sterilized and packed in a protective envelope 5, as illustrated in FIGS. 10 to 12. The insertion cup 3 is packed separately.

To use the acetabulum, the practitioner selects an insertion cup 3 suitable for the morphology of the cotyloid cavity formed in the patient who is to be treated, chooses an assembly of articular insert 1 and spherical head 2 whose recess 2c is suitable for adjusting the length of the first part of a prosthesis as a function of the anatomical features of the patient who is to be treated, places the insertion cup 3 in the cotyloid cavity formed in the pelvis of the patient, and assembles the other elements of the hip prosthesis without first having to fit the spherical head 2 with force into the articular insert 1.

Figure 13:
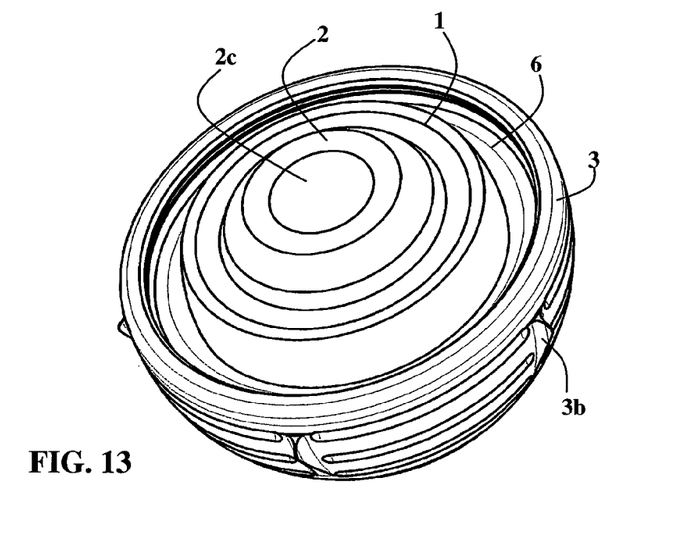
FIGS. 13 to 15 illustrate, in a perspective view, a front view and a lateral cross section, respectively, a prosthetic hip acetabulum according to a second embodiment of the present invention.
Figure 14:
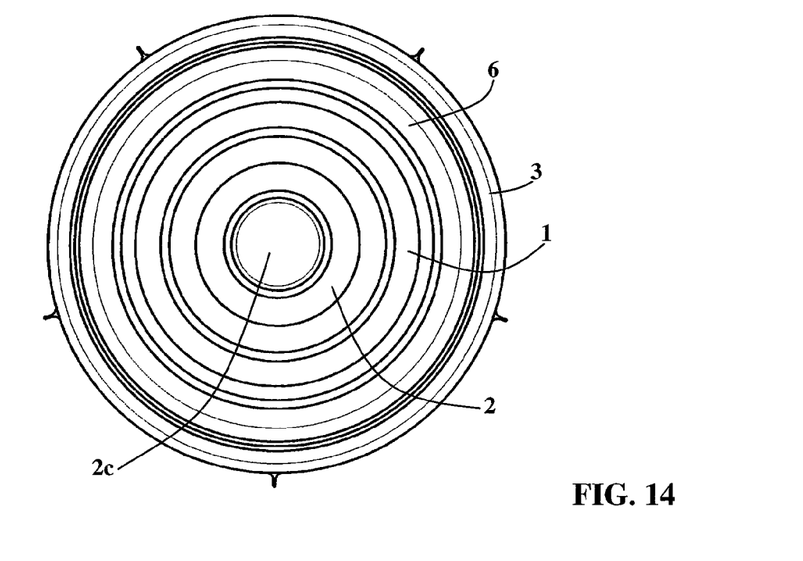
Figure 15:
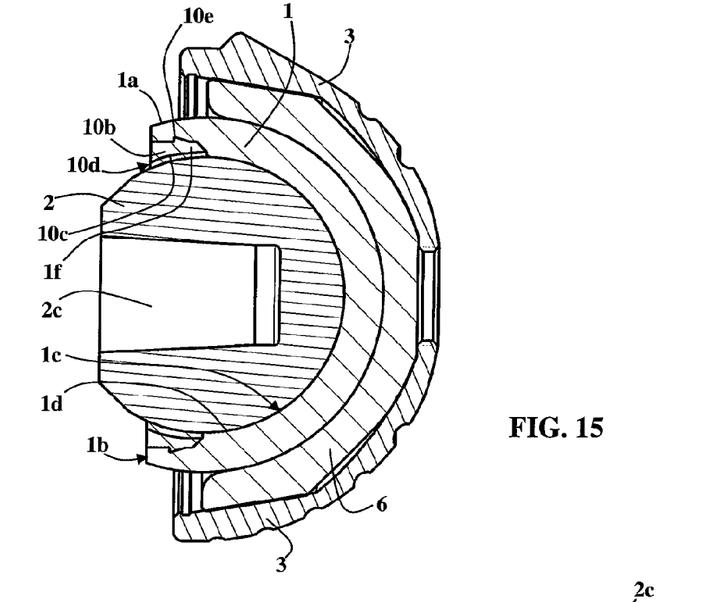

A second embodiment of a prosthetic hip acetabulum according to the invention, as illustrated in FIGS. 13 to 15, is now described.

This embodiment again has an articular insert 1 receiving and retaining a spherical head 2. The articular insert 1 is engaged with rotation in an intermediate insert 6, which is itself engaged fixedly in an insertion cup 3.

In this embodiment, the spherical head 2, the articular insert 1 and the intermediate insert 6 can be made of ceramic. The insertion cup 3 is made of metal, for example stainless steel or titanium.

The spherical head 2 has the same shape as the head 2 in the embodiment in FIGS. 1 to 12.

The articular insert 1 is similar to the one in the preceding embodiment in FIGS. 1 to 12 in that it again has the articular surface 1d, the articular cavity 1c, in which the spherical head 2 is engaged, the receiving face 1b, and the spherical outer surface 1a.

The difference in this second embodiment lies essentially in the structure of the retaining means.

In this case, the retaining means comprises a continuous annular ring 10b, having a retaining surface 10c in the shape of a spherical crown able to engage functionally with play 10d against the spherical head 2 and having peripheral fixing projections 10e able to interlock functionally with corresponding recesses if of the articular insert 1.

In practice, the continuous annular ring 10b is engaged in a seat of corresponding shape formed at the entrance of the articular cavity 1c of the articular insert 1. The peripheral projections 10e comprise, for example, a peripheral rib of the continuous annular ring 10b, which rib engages in a corresponding annular groove of the articular insert 1. When the continuous annular ring 10b is placed in the articular insert 1, its retaining surface 10c constitutes an undercut segment which retains the spherical head 2 inside the articular cavity 1c of the articular insert 1.

As in the embodiment in FIGS. 1 to 12, the articular insert 1 and the spherical head 2 are delivered in an assembled and sterile state in a protective envelope, with the continuous annular ring 10b in place, such that, when the prosthesis is being implanted, the practitioner does not have to fit the head 2 with force into the articular insert 1.

Figure 16:
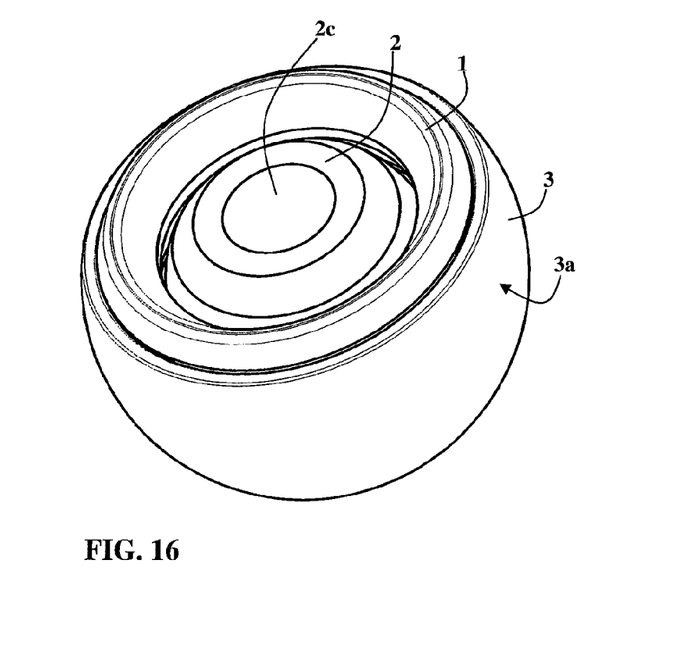
FIGS. 16 to 18 illustrate, in a perspective view, a front view and a lateral cross section, respectively, a prosthetic acetabulum of the movable cup type according to a third embodiment of the present invention.
Figure 17:
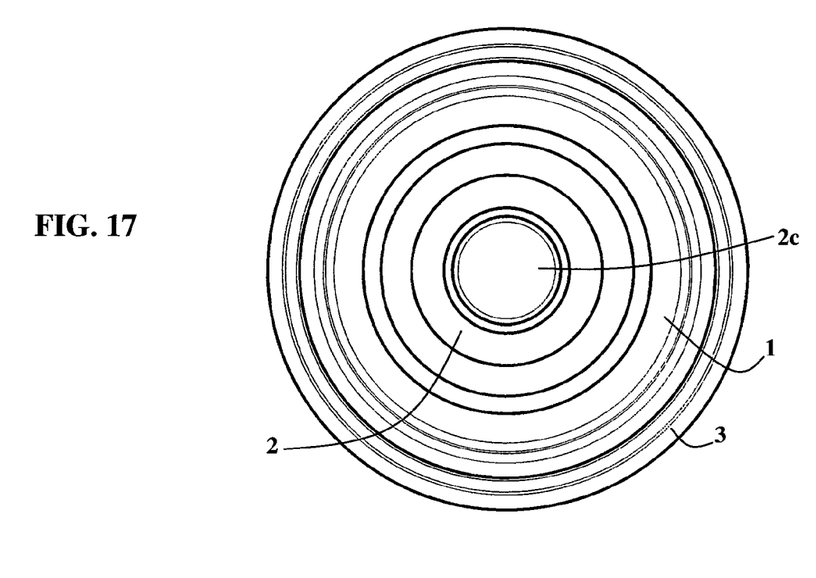
Figure 18:
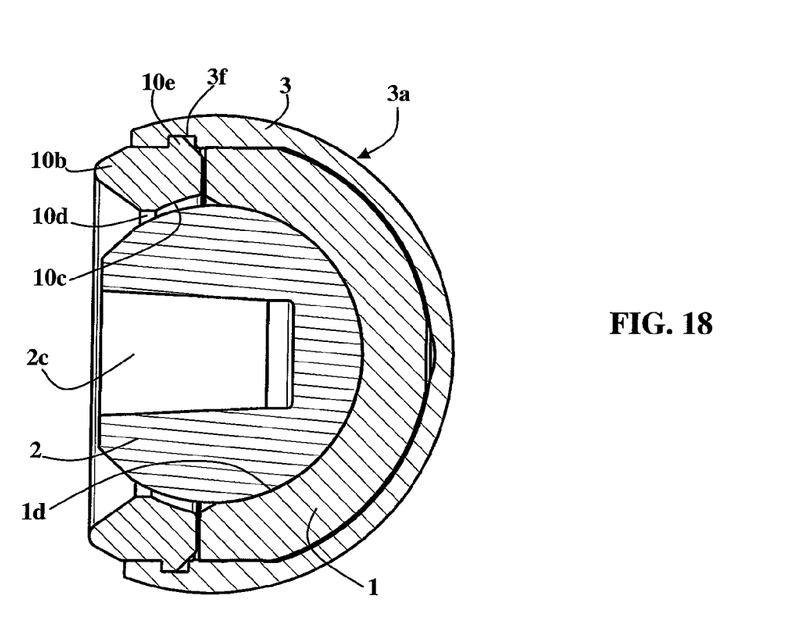

A third embodiment of a prosthetic hip acetabulum according to the invention is now described, as illustrated in FIGS. 16 to 18. This once again has a spherical head 2, identical to the head in the preceding embodiment, an articular insert 1 and a cup 3. A first difference lies in the fact that the cup 3 is a movable cup whose outer face 3a is spherical and smooth in order to constitute a sliding surface that can be engaged and pivoted in the cotyloid cavity of a patient.

In this embodiment, the articular surface 1d of the articular insert 1 is hemispherical. The articular insert 1 is made of polyethylene or another equivalent plastic material and is engaged fixedly in the cup 3. The retaining means is once again a continuous annular ring 10b, similar to the one in the embodiment in FIGS. 13 to 15, with a retaining surface 10c in the shape of a spherical crown that is able to engage functionally with a play 10d against the spherical head 2, and having peripheral fixing projections 10e.

In this case, the peripheral projections 10e lock themselves in recesses 3f formed in the cavity of the cup 3. Thus, the continuous annular ring 10b is retained by the cup 3. Its retaining surface 10c in the shape of a spherical crown constitutes an undercut segment of the articular surface 1d, which opposes the withdrawal of the spherical head 2 from the articular insert 1.

Figure 19:
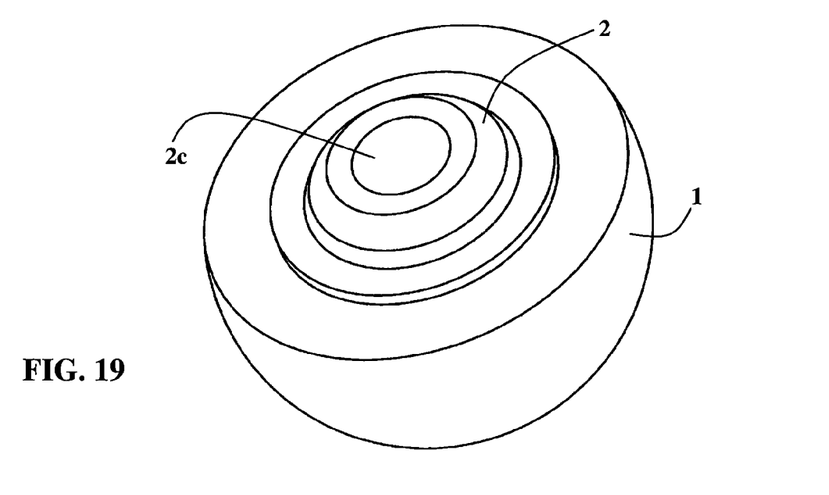
FIGS. 19 to 21 illustrate, in a perspective view, a front view and a lateral cross section, respectively, a prosthetic hip acetabulum of the movable cup type according to a fourth embodiment of the present invention.
Figure 20:
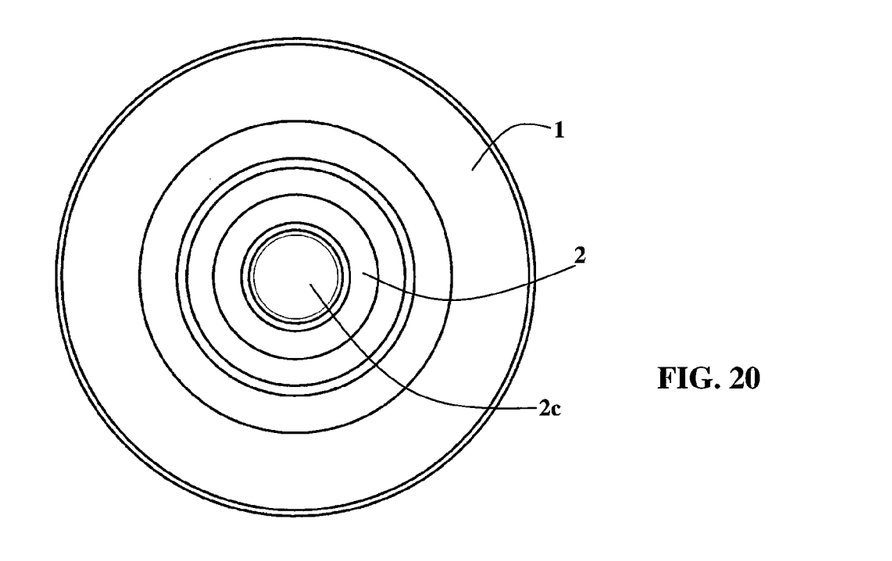
Figure 21:
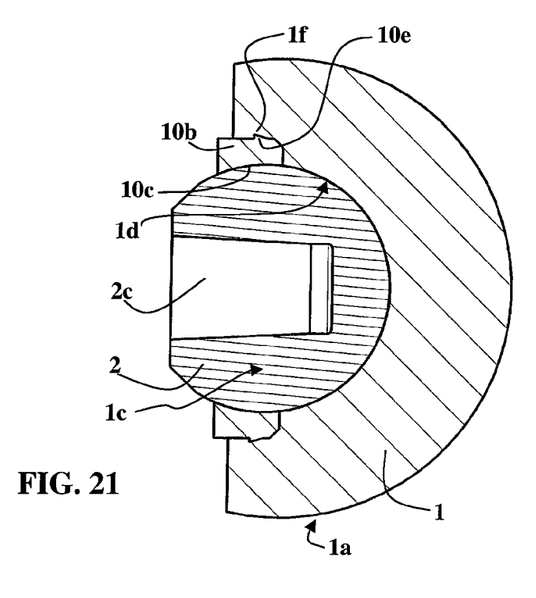

FIGS. 19 to 21 illustrate a fourth embodiment of a prosthetic hip acetabulum according to the invention. This once again has a spherical head 2 identical to those of the preceding embodiments. The articular insert 1 is made of ceramic and has a substantially hemispherical articular surface 1d. The outer surface 1a of the articular insert 1 made of ceramic is spherical, so as to constitute an articular surface that is able to pivot in a cotyloid cavity in the pelvis of the patient.

In this embodiment, the retaining means is once again formed by a continuous annular ring 10b made of polyethylene or another equivalent plastic material, with a retaining surface 10c in the shape of a spherical crown forming an undercut segment of the articular surface 1d, and with peripheral fixing projections which lock functionally with corresponding recesses if of the articular insert 1. An acetabulum with a movable cup made of ceramic is thus obtained.

Figure 22:
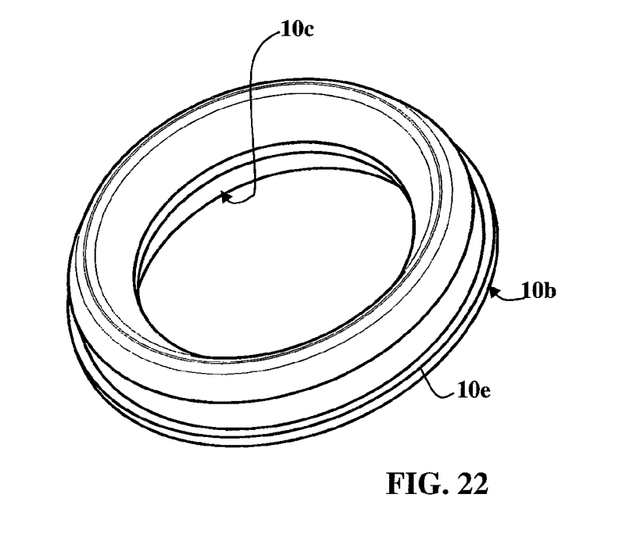
FIG. 22 illustrates, in a perspective view, a continuous annular ring.

FIG. 22 illustrates, in a perspective view, the continuous nature of the annular ring 10b, the latter being like the rings used in the embodiments in FIGS. 13 to 21.

In all the embodiments that have been described, the retaining means is a component made of polyethylene or of equivalent plastic material, which component has to be deformed when fitting the spherical head 2 into the articular insert 1. It is possible, for example, to use polyethylene, polyether ether ketone (PEEK), etc.

In the embodiment in FIGS. 1 to 3, it is necessary to deform the mouth of the articular insert 1 in order to expand it and thereby facilitate the insertion of the spherical head 2.

In the other embodiments, it is necessary to contract the continuous annular ring 10b in order to facilitate its engagement in the articular insert 1 or in the peripheral cup 3.

For this purpose, the retaining means is subjected to a differential thermal stress which temporarily modifies its dimensions and thus facilitates its assembly. After assembly, the retaining means is allowed to return to room temperature, such that it recovers its original shape and then opposes the withdrawal of the spherical head 2 from the articular insert 1.

In the embodiment in FIGS. 1 to 3, in which the articular insert 1 itself constitutes the retaining means 10a and is made of polyethylene, the differential thermal stress consists in heating the articular insert 1 in order to temporarily increase its internal diameter and thereby facilitate the axial introduction of the spherical head 2.

In the case of a retaining means in the form of a continuous annular ring 10b, the differential thermal stress consists in cooling the continuous annular ring 10b in order to temporarily reduce its external diameter and thereby facilitate the engagement of the peripheral projections 10e of the ring in the corresponding recesses 1f or 3f, respectively, of the articular insert 1 or the peripheral cup 3.

According to the invention, the assembly step as defined above is performed before the step of sterilizing the unit composed of spherical head 2 and articular insert 1.

The sterilizing step can comprise a step of sterilization by bombardment with gamma rays.

It has been found, according to the invention, that assembly prior to sterilization allows the retention capacity of the spherical head in the articular insert to be substantially increased, which reduces the risks of luxation.

This increasing of the retention capacity has been demonstrated by carrying out comparative traction tests on a head engaged in an articular insert, under the following conditions:
  head made of stainless steel measuring 28 mm;
  articular insert made of polyethylene, with an undercut retaining segment measuring 4 mm in length, and with an external diameter of 48, 54 or 62 mm;
  axial traction force exerted between the head and the articular insert.

The table below shows the limit values of the force bringing about the release of the spherical head from the articular insert for the three external diameters of the articular insert and in each of two cases: head introduced into the articular insert after sterilization, or head introduced into the articular insert before sterilization:

| Insert diameter | Force producing withdrawal of a head impacted after sterilization (in daN) | Force producing withdrawal of a head impacted before sterilization (in daN) |
| --- | --- | --- |
| 48 | 42.71 | 50.10 |
| 54 | 54.01 | 65.32 |
| 62 | 65.21 | 73.03 |

The present invention is not limited to the embodiments that have been explicitly described and instead it includes the various modifications and generalizations contained within the scope of the attached claims.

The invention claimed is:

1. A method of making a prosthetic hip acetabulum, comprising the steps of:
  a) providing a set of components including:
    i) an articular insert (1), with a receiving face (1b) in which is opened a cavity (1c) with a substantially hemispherical, concave articular surface (1d),
    ii) a spherical head (2), which can be engaged in the articular cavity (1c) of the articular insert (1), and
    iii) a retaining means (10a, 10b) for opposing the axial release of the spherical head (2) from the articular cavity (1c) of the articular insert (1) when it is engaged in the articular cavity (1c), wherein the retaining means is made of polyethylene,
  b) assembling said components such that the spherical head (2) is engaged in the articular cavity (1c) of the articular insert (1) and is retained by the retaining means (10a, 10b), and
  c) after completion of step (b), sterilizing the assembled components.

2. The method of claim 1, wherein step b) includes engaging the spherical head (2) across a spherical cap (2b) larger than the hemisphere.

3. The method of claim 2, further comprising configuring the spherical cap (2b) to extend by an angle (A) greater than 190°.

4. The method of claim 1, wherein the retaining means (10a, 10b) is formed by the articular insert (1) itself, and has a retaining segment (10a) undercut in the articular surface (1d).

5. The method of claim 4, wherein the articular insert (1) has an outer surface (1a) in the shape of a spherical cap in order to be mounted rotatably in an insertion cup (3) and in order thereby to constitute a dual-mobility acetabulum.

6. The method of claim 1, wherein the retaining means comprises a continuous annular ring (10b), having a retaining surface (10c) in the shape of a spherical crown able to engage functionally with play (10d) against the spherical head (2), and having peripheral fixing projections (10e) able to interlock functionally with corresponding recesses (1f) of the articular insert (1) or with corresponding recesses (3f) of a peripheral cup (3) surrounding the articular insert (1), in order to prevent withdrawal of the continuous annular ring (10b).

7. The method of claim 1, wherein step (b) includes subjecting the retaining means (10a, 10b) to a differential thermal stress which temporarily modifies its dimensions in order to facilitate assembly, and then, after assembly, allowing the retaining means to return to room temperature so as to then oppose withdrawal of the spherical head (2) from the articular insert (1).

8. The method of claim 7, wherein the subjecting step includes heating the articular insert (1) in order to increase its internal diameter and thereby facilitate the axial introduction of the spherical head (2).

9. The method of claim 7, wherein the retaining means comprises a continuous annular ring (10b), and wherein the subjecting step includes cooling the continuous annular ring (10b) in order to reduce its internal diameter and thereby facilitate the engagement of peripheral projections (10e) of the ring (10b) in corresponding recesses (1f, 3f) of the articular insert (1) or of a peripheral cup (3).

10. The method of claim 1, wherein step b) includes forcibly engaging one component in another.

* * * * *